United States Patent [19]

Woodward

[11] Patent Number: 5,093,329

[45] Date of Patent: Mar. 3, 1992

[54] INTRAOCULAR PRESSURE REDUCING PROSTAGLANDIN-LIKE 7-OXABICYCLO DERIVATIVES

[75] Inventor: David A. Woodward, El Toro, Calif.

[73] Assignee: Allergan, Inc., Irvine, Calif.

[21] Appl. No.: 492,620

[22] Filed: Mar. 12, 1990

[51] Int. Cl.$^5$ .............................................. A61K 31/34
[52] U.S. Cl. ..................................... 514/469; 514/913
[58] Field of Search ................................ 514/469, 913

[56] References Cited

U.S. PATENT DOCUMENTS

| | | | |
|---|---|---|---|
| 4,537,981 | 8/1985 | Snitman et al. | 549/463 |
| 4,654,366 | 3/1987 | Varma et al. | |
| 4,673,685 | 1/1987 | Varma et al. | |

OTHER PUBLICATIONS

Chem. Abst. 102:1050c (1985), Harris et al.

*Primary Examiner*—Frederick E. Waddell
*Assistant Examiner*—Zohreh Fay
*Attorney, Agent, or Firm*—Robert J. Baran; Martin A. Voet

[57] ABSTRACT

Disclosed are a method and composition for treating ocular hypertension. The compositions comprise prostaglandin-like 7-oxabicyclo derivatives which have been discovered to exhibit a pronounced intraocular pressure reducing effect, but with substantially reduced adverse side effects characteristic of the corresponding prostaglandin.

10 Claims, No Drawings

INTRAOCULAR PRESSURE REDUCING PROSTAGLANDIN-LIKE 7-OXABICYCLO DERIVATIVES

BACKGROUND OF THE INVENTION

The present invention relates to compositions of matter for reducing or maintaining intraocular pressure, and, more particularly, to a method and composition for reducing or maintaining intraocular pressure involving the administration of a composition of matter containing a prostaglandin-like 7-oxabicyclo derivative in a pharmaceutically acceptable carrier.

The compositions and method of the present invention are particularly useful for the management of glaucoma, a disease of the eye characterized by increased intraocular pressure. On the basis of its etiology, glaucoma has been classified as primary or secondary. For example, primary glaucoma in adults, e.g., congenital glaucoma, may be either chronic open-angle, or acute or chronic angle-closure. Secondary glaucoma results from pre-existing ocular disease, typically such as uneitis, intraocular tumor or an enlarged cataract.

The causes of primary glaucoma are not yet known. The increased intraocular tension is related to an imbalance between production and outflow of the aqueous humor, typically due to obstruction to outflow. In chronic open-angle glaucoma, the anterior chamber and its anatomic structures appear normal but draining of the aqueous humor is impeded. In acute and chronic angle-closure glaucoma, the anterior chamber is shallow, the filtration angle is narrowed and the iris may obstruct the trabecular meshwork at the entrance of the canal of Schlemm. Dilation of the pupil may push the root of the iris forward against the angle or may produce pupillary block and thus precipitate an acute attack. Eyes with narrow anterior chamber angles are predisposed to acute angle-closure glaucoma attacks of varying degrees of severity.

Secondary glaucoma is caused by an interference with the flow of aqueous humor from the posterior chamber into the anterior chamber to the canal of Schlemm. Inflammatory disease of the anterior segment may prevent aqueous escape by causing complete posterior synechia in iris bombe, and may plug the draining channel with exudates. Other common causes are intraocular tumors, enlarged cataracts, central retinal vein occlusion, trauma to the eye, operative procedures and intraocular hemorrhage.

Considering all types together, glaucoma occurs in about 2% of all patients over the age of 40, and may be asymptomatic for years before progressing to rapid loss of vision. In cases where surgery is not indicated, systemic and topical β-adrenoceptor antagonists have traditionally been the drugs of choice for treatment. Certain eicosanids, particularly various prostaglandins, have been reported to possess hypotensive activity. However, prostaglandin ocular hypotensives generally suffer from the disadvantage of inducing conjunctival hyperemia of varying severity and duration, smarting and foreign body sensation, as well as presenting solubility problems in certain ophthalmically advantageous carriers.

The present invention relates to certain prostaglandin-like 7-oxabicyclo derivatives which may be formulated in a pharmaceutically acceptable vehicle, and ophthalmic uses of those prostaglandin compositions. The formulations of the present invention have been discovered to retain an intraocular pressure reducing effect similar to that of the related prostaglandin, but with elimination of the aforementioned undesirable side effects.

The compounds are known (U.S. Pat. No. 4537981) and may be synthesized by methods known in the art for the synthesis of compounds of analogous structure. They have been previously reported as having potential utility in cardiovascular and respiratory diseases. Their safe use as ocular hypotensives is unexpected and previously unrecognized.

SUMMARY OF THE INVENTION

In accordance with one aspect of the present invention, there is provided a pharmaceutical formulation comprising an ophthalmically acceptable carrier together with at least one compound of the formula (I)

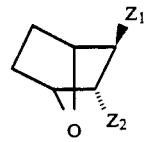

wherein $Z_1$ is an $RCOOR_1$ group in the $\beta$ configuration, wherein R is an alkyl or alkenyl group having up to 10 and preferably 4–8 carbon atoms, $R_1$ is H, (to produce the free acid form) or any cation which together with the parent compound forms a pharmaceutically acceptable salt, or $R_1$ is an aliphatic radical of from one to ten carbon atoms; $Z_2$ is $-CH=CH-CH(OR_2)R_3$ in the $\alpha$ configuration wherein $R_2$ is H or an acyl group having from one to six carbon atoms and $R_3$ comprises a cycloalkyl or aryl moiety having five or six carbon atoms, and, preferably is cycloalkyl or benzyl most preferably cyclohexane.

In a preferred aspect of the present invention, $Z_1$ is $(CH_2)_6 COOH$ and $Z_2$ is

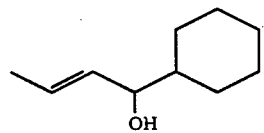

In accordance with a further aspect of the present invention, there is provided a method of treating ocular hypertension, which comprises administering to a mammal having ocular hypertension an amount effective for treating hypertension of a composition as defined above.

Further features and advantages of the present invention will become apparent from the detailed description of preferred embodiments which follows, taken together with the Examples and Claims.

DETAILED DESCRIPTION OF THE PREFERRED EMBODIMENTS

A variety of prostaglandins are known and have been shown to exhibit a wide variety of biological activity. The compounds referred to generally as prostaglandins are analogs of prostanoic acid, the structure of which is as follows:

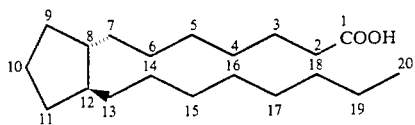

Prostaglandins have been classified as existing in several main forms, designated by letters and distinguished by substitutions on the cyclopentane ring. For example, the prostaglandins A-F have cycopentane constituents as follows:

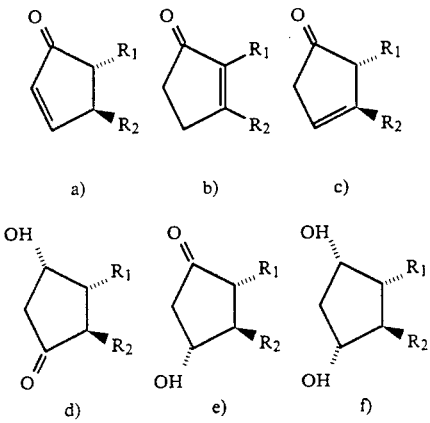

For thromboxane $A_2$ (TxA$_2$) the cyclopentane ring undergoes oxygen insertion to form a bicyclo structure as follows:

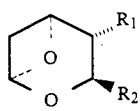

In addition, these major classes of prostanoids have been further subdivided according to the number of double bonds existing on the side chains. This number is indicated by the subscript 1, 2 or 3, which reflects the fatty acid precursor. Thus, for example, prostaglandins derived form 8, 11, 14-eicosatrienoic acid carry the subscript 1. Those derived from arachidonic acid carry the subscript 2, and those derived form 5, 8, 11, 14, 17-eicosapentaeonic acid carry the subscript 3.

PGD class of prostaglandins, for example, has the following abbreviated nomenclature and structure:

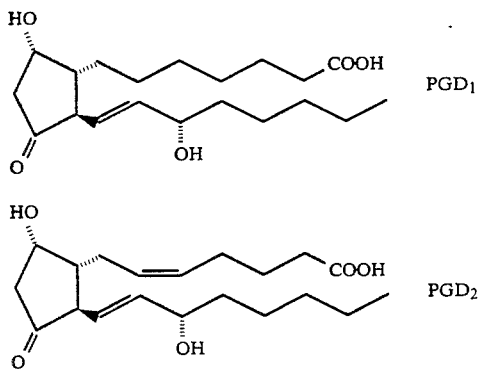

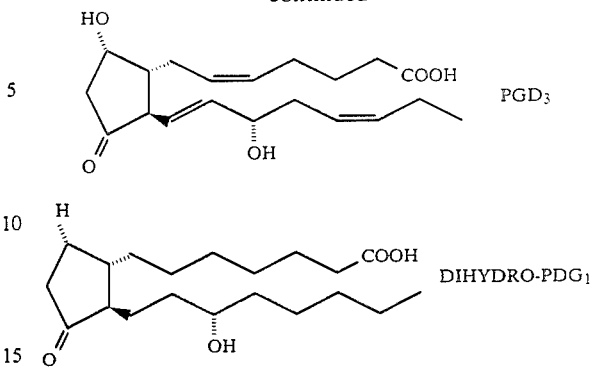

In all of the foregoing illustrations, as well as those provided hereinafter, broken line attachments to the cyclopentane or cycloheptane ring indicate substituents in the alpha configuration. Thickened solid line attachments to the cyclopentane or cycloheptane ring indicate substituents in the beta configuration. Also, the broken line attachment of the hydroxyl group to the C-15 carbon atom signifies the alpha configuration; therefore, compounds with the epi configuration for the hydroxyl group at C-15 are designated by using 15-beta (15-$\beta$) and if there is no indication of the beta configuration, the configuration is assumed to be alpha.

Prostanoids are naturally occurring metabolites of arachidonic acid (5, 8, 11, 14-eicosatetraenoic acid). The fatty acid cycloxygenase sequentially transforms arachidonic acid into the cyclic endoperoxides, prostaglandin $G_2$ (PGG$_2$) and $H_2$ (PGH$_2$) which are short lived, (t ½-5 min. at 37° C. and pH 7.5) common intermediates in the synthesis of prostanoids. Prostaglandin H$_2$ may in turn be isomerized into either prostaglandin D$_2$ (PGD$_2$), or reduced to $F_{2\alpha}$ (PGF$_{2\alpha}$) or be converted to thromboxanes by thromboxane synthetase, or to prostacyclin (PGI$_2$) by prostacyclin synthetase.

It has been discovered that certain prostaglandins lower intraocular pressure in man and other mammals when applied topically to the cornea. Although the precise mechanism is not yet known, they appear to increase aqueous humor outflow to restore a normotensive or hypotensive state. However, topical application of prostanoids generally produces side effects such as conjunctival hyperemia, smarting, foreign body sensations, and inflammation which range in degree from undesirable to unacceptable, depending upon the particular patient and dosage necessary to produce a sufficient pressure regulating effect.

Thus, although prostaglandin D$_2$ (PGD$_2$) has been discovered to potently lower intraocular pressure (IOP), it would generally be unsuitable for treating ocular hypertensive diseases due to the relative severity of resulting inflammatory effects on the conjunctiva. The PGD-like 7-oxabicyclo derivatives of the present invention provide an unexpected means of retaining PGD$_2$-like effects in IOP without ocular surface inflammation. The basis for this separation of effects is described as follows.

PGD$_2$ causes a wide spectrum of biological effects, but recent studies reveal that these effects may be separated according to structural modification of PGD$_2$. A profile of activity in PGD$_2$-sensitive tissues that appears particularly useful for predicting PGD$_2$ analogs that are potent ocular hypotensives without causing ocular surface side effects is retention of anti-aggregatory activity in platelets by a mechanism that involves stimulation of the DP-receptor for PGD$_2$. Representative compounds of this category which have been found to exemplify the advantage of such analogs include prostaglandin-like compounds having the following heterocyclic structure:

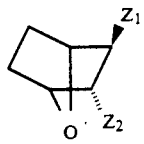

which have been found to lower IOP over a 0.01–0.1% dose-range but do not cause ocular surface pathology or hyperemia at doses that enormously exceed their expected therapeutic doses. The concept that the utility of the present invention resides in stimulation of a particular subset of PGD$_2$-mimetic does not significantly lower IOP but retains the proinflammatory aspects of PGD$_2$ on the conjunctiva.

Thus, in accordance with one aspect of the present invention, there is provided a pharmaceutical formulation comprising a pharmaceutically acceptable carrier together with at least one compound having the structure of formula (I), in which $Z_1$ and $Z_2$ are as hereinabove defined.

In a preferred aspect of the present invention, $Z_1$ is RCOOR$_1$, wherein R is an alkenyl having 6 carbon atoms, and R$_1$ is H to produce the free acid form, or any cation which together with the parent compound forms a pharmaceutically acceptable salt, or R$_1$ is an aliphatic radical of from one to ten carbon atoms.

Suitable pharmaceutically acceptable salts may be derived from either an organic or inorganic base. Such salt may comprise a mono- or polyvalent ion. Of particular interest are inorganic cations such as sodium, potassium, calcium and magnesium. Organic salts may be made with amines, particularly ammonium salts such as mono-, di- and trialkyl amines or ethanol amines. Salts may also be formed with caffeine tromethamine and similar molecules. Where acid addition salts are formed from amines, any inorganic or organic acid may be used. Preferred salts are hydrogen chloride salts, sulfate salts, phosphate salts and salts of simple organic acids of 2 to 6 carbons, either the mono- or diacids. Quaternary ammonium compounds can be prepared from alkylating agents such as methyl iodide and the like.

$Z_2$ is —CH=CH—CH(OR$_2$)R$_3$ wherein R$_2$ is H or an acyl group having from one to six carbon atoms. Preferably, R$_3$ comprises a cyclic moiety, having five or six carbon atoms, and, preferably is benzyl or cyclohexane, most preferably cyclohexane.

The term "alkyl" is used to refer to saturated, straight or branched chained aliphatic hydrocarbon groups. Typical alkyl representatives of the alkyl groups are, for example, methyl, ethyl, n- and isopropyl, n-, sec-, iso- and terc-butyl, n- and isopentyl, n- and neo-hexyl, n- and isooctyl, etc. Typical alkenyl groups are vinyl, butenyl, propenyl, etc.

The term "aryl" alone or as part of an aralkyl group, refers to aromatic hydrocarbon groups that may contain one or more heteroatoms, such as oxygen sulfur, nitrogen. The alkyl moiety in the aralkyl groups typically has up to 6, preferably up to 4 carbon atoms.

The term "therapeutically effective amount" as used herein, refers to sufficient quantities of the active compound that can produce the desired therapeutic effect (ocular hypotensive action) when delivered through the cornea and sclera at the location of application. The selection of optimal dose for the treatment of a certain ocular condition is well within the knowledge of a skilled physician. The typical daily dose is 1 drop/eye up to 8-times a day, preferably up to 4-times a day.

The pharmaceutical compositions of the present invention preferably are in the form of ophthalmic solutions, typically containing from about 0.0001% to about 10%, preferably from about 0.001% to about 5%, more preferably from about 0.01% to about 0.1% active ingredient, and a physiological saline solution as a major vehicle. The pH of such ophthalmic solutions should preferably be maintained between about 6.5 and about 7.2 with an appropriate buffer system. The formulations may also contain conventional pharmaceutically acceptable preservatives, stabilizers and/or penetration enhancers. In accordance with a preferred embodiment, the carrier comprises a solution having polysorbate 80–10 mM TRIS in the range of from about 0.05–1.0% by weight, and preferably about 0.1%, which is particularly suited for administration in the form of liquid eye drops.

The ophthalmic formulations of the present invention are conveniently packaged in forms suitable for metered application, such as in containers equipped with a dropper, to facilitate application to the eye. Containers suitable for dropwise application are usually made of a suitable inert, non-toxic plastic material, and generally contain between about 0.5 ml and about 15 ml solution. Examples are presented as follows:

EXAMPLE 1

[1β,2β(5Z),3α(1E,3S*),4β]-7-[3-Cyclohexyl-3-hydroxy-1-propenyl)-7-oxabicyclo[2.2.1]hept-2-yl]-5-heptenoic acid

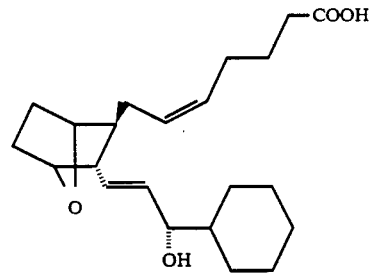

A. [1β,2β(5Z),3α,4β]-7-[3-Formyl-7-oxabicyclo[2.2.1]-hept-2-yl]-5-heptenoic acid, methyl ester A solution of pyridine (8.7 ml) in dichloromethane (200 ml) is treated portionwise with chromium trioxide (5.38 g) with vigorous stirring. After addition is complete, the mixture should be stirred at room temperature for 20 minutes, treated with celite (8 g) and then the [1β,2β(5Z),3β,4β]-7-[3-(hydroxymethyl)-7-oxabicyclo[2.2.1]hept-2-yl]-5-heptenoic acid, methyl ester is prepared as described in U.S. Pat. No. 4,143,054 (2,58 g, 0.0096 moles) in dichloromethane (10 ml). The reaction mixture is stirred at room temperature for 20 minutes then filtered through celite. The filtrate is washed with 5% sodium bicarbonate (2×100 ml), 10% hydrochloric acid (2×100 ml) and again with 5% sodium bicarbonate (2×100 ml). The dichloromethane solution is dried over magnesium sulfate and concentrated in vacuo. The residue should be chromatographed on silica gel CC-7 (200 ml) eluting with 1) dichloromethane and 2) diethyl ether to yield 2 g of aldehyde. The product is a mixture of isomers (90% cis-endo and 10% trans-aldehyde). Drying in vacuo at room temperature for any extended period of time causes decomposition as evidenced by thin layer chromatography, TLC: silica gel; benzene/EtOAc(4:1) $R_f$=0.5; visualized with vanillin spray and heat.

B. [1β,2β(5Z),3α(1E),4β]-7-[3-(3-Oxo-3-cyclohexyl-1-propenyl)-7-oxabicyclo[2.2.1]hept-2-yl]-5-heptenoic acid, methyl ester To a slurry of 180 mg of 50% sodium hydride (3.75 mmole, 1.44 equivalents) in 60 ml of anhydrous dimethoxyethane (DME) is added 870 mg of 2-oxo-2-cyclohexylethyldimethylphosphonate (3.75 mmole, 1.44 equivalents) in 10 ml of dimethoxyethane at 0° C. under an argon atmosphere. The mixture is stirred at 25° C. for 1.5 hours. To this solution at 25° C. is added 700 mg of [1β,2β(5Z),3α,4β)]-7-[3-formyl-7-oxabicyclo[2.2.1]-hept-2-yl]-5-heptenoic acid, methyl ester (2.6 mmol) in 10 ml of dimethoxyethane. After 1 hour, the reaction is quenched with 0.5 ml of glacial acetic acid, concentrated, dissolved in 200 ml of ether and washed with 150 ml of 5% potassium bicarbonate, dried over anhydrous magnesium sulfate and concentrated. The residue may be purified by flash chromatography on LP-1 silica gel, eluting with 3:7 ether/hexane to provide 515 mg (52% yield) of the title β compound.

$C_1$. [1β,2β(5Z),3α(1E,3S*),4β]-7-[3-(3-Cyclohexyl-3-hydroxy-1-propenyl)-7-oxabicyclo[2.2.1]hept-2-yl]-5-heptenoic acid, methyl ester and $C_2$. [1β,2β(5Z)3α(1E,3R*),4β]-7-[3-(3-Cyclo hexyl-3-hydroxy-1-propenyl)-7-oxabicyclo[2.2.1]hept-2-yl]-5-heptenoic acid, methyl ester To a solution of 515 mg of the title βcompound (1.38 mmole) in 15 ml of dry methanol is added at 25° C. under an argon atmosphere 513 mg of cerium chloride hepahydrate (1.38 mmole, 1 equivalent). The reaction is stirred for 10 minutes, cooled to 0° C. and 53.2 mg of sodium borohydride (1.38 mmole, 4 equivalents) is added. After stirring for 20 minutes at 0° C. the reaction is quenched with 1 ml of acetone, concentrated under high vacuum, diluted with 100 ml of ethyl acetate and washed with 100 ml of brine. The aqueous layer is reextracted with 100 ml of ethyl acetate. The combined organic layers are dried over anhydrous magnesium sulfate and concentrated. The residue is purified by flash chromatography on LP-1 silica gel column, eluting with 1:4 EtOAc-hexane to give 210 mg of the title $C_1$ compound and 191 mg of the title $C_2$ compound.

D. [1β,2β(5Z)3α(1E,3S*),4β]-7-[3-(3-Cyclohexyl-3-hydroxy-1-propenyl)-7-oxabicyclo[2.2.1]hept-2-yl]-5-heptenoic acid. 200 mg of the title $C_1$ alcohol ester (0.53 mmole) is dissolved in 30 ml of an 80% tetrahydrofuran-water solution, chilled to 0° C., and 5.3 ml of a 1N Lithium hydroxide solution is added dropwise. The reaction mixture is stirred at 0° C., then slowly warmed to 25° C. and stirred for 18 hours. The THF is evaporated under high vacuum and the residue is diluted with 10 ml of water, acidified to pH 3 with a 10% aqueous oxalic acid solution, extracted with three 60 ml portions of ether and 50 ml of brine. The product is dried over anhydrous magnesium sulfate and concentrated to give an oil.

This oil is purified on CC7 silica gel, eluting with a gradient of distilled pentane/ether and filtered through a polycarbonate membrane. The solvents may be evaporated under high vacuum for 10 days to give 165 mg of the title compound (86%).

TLC:silica gel; EtOAc/hexane (4:1 $R_f$~0.58).

EXAMPLE 2

[1β,2β(5Z)3α(1E,3,S°),4β]-7-[3-(3-Hydroxy-4-phenyl-1-buten-yl)-7-oxabicyclo[2.2.1]hept-2-yl]-5-heptenoic acid

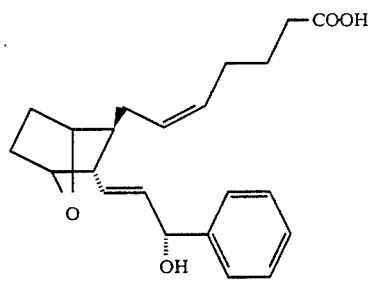

A. [1β,2β(5Z)3α(1E,4β]-7-[3-(3-Oxo-4-phenyl-1-butenyl)-7-oxabicyclo[2.2.1]hept-2-yl]-5-heptenoic acid, methyl ester To 411.6 mg of freshly distilled diisopropylamine in 80 ml of dry toluene at −78° C. add 2.3 ml of a 1.6M solution of n-butyllithium in hexane (3.71 mmole). The mixture is stirred for 5 minutes, and to this mixture at −78° C. is added 952.5 mg of 2-oxo-3-phenyl-propyl-dimethylphosphonate (3.91 mmole, 1.1. equivalent). The mixture is warmed up to 25° C. while stirring. To this mixture at 25° C. is added 938 mg of [1β,2β(5Z)3α,4β]-7-[3-formyl-7-oxabicyclo[2.2.1]hept-2-yl]-5-heptenoic acid, methyl ester prepared as described in Example 1, part A (3.55 mmole). After 2.5 hours, the reaction is quenched with 0.5 ml of glacial acetic acid and diluted with 300 ml of ether. The ethereal solution is washed with three 100 ml portions of 5% sodium bicarbonate solution and 100 ml of brine. The organic layer is dried over anhydrous magnesium sulfate and concentrated to give 1.22 g of a crude oil. This oil is used in the next step without purification.

B. [1β,2β(5Z)3α(1E,3S*),4β]-7-[3-(3-Hydroxy-4-phenyl-1-butenyl)-7-oxabicyclo[2.2.1]hept-2-yl]-5-heptenoic acid, methyl ester and C. [1β,2β(5Z)3α(1E,3R*),4β]-7-[3-(3-Hydroxy-4-phenyl-1-butenyl)-7-oxabicyclo[2.2.1]hept-2-yl]-5-heptenoic acid, methyl ester To a solution of 1.22 g of the crude title A compound in 30 ml of dry methanol is added, at 25° C. under an argon atmosphere, 1.18 g of cerium chloride containing 35% water (2.64 mmole, 1 equiv.). The reaction is stirred for 10 minutes at 25° C., cooled to 0° C., and 119 mg of sodium borohydride (2.64 mmole, 4 equiv.) is slowly added. After stirring for 10 minutes at 0° C., the reaction is poured into 200 ml of saturated ammonium chloride. The mixture is extracted with three 100 ml portions of ether. The etheral extracts are washed with three 100 ml portions of water and 100 ml of brine. The organic layer is dried over anhydrous magnesium sulfate and concentrated. Separation and purification is achieved by HPLC eluting with 30% ethylacetate in hexane to give 299 mg of the title β compound and 272 mg of the title C compound.

TLC of title β: Silica gel; EtOAc/hexane (1:1); $R_f$~0.44.

TLC of title C: $R_f$~0.35.

D. [1β,2β(5Z)34(1E,3S*),4β]-7-[3-(3-Hydroxy-4-phenyl-1-butenyl)-7-oxabicyclo[2.2.1]hept-2-yl]-5-heptenoic acid 299 mg of the title β alcohol ester (0.78 mmole) is dissolved in 50 ml of an 80% tetrahydrofuran-water solution, chilled to 0° C., and 7.8 ml of 1N lithium hydroxide solution is added dropwise. The reaction mixture is stirred at 0° C., then slowly warmed up to 25° C. over a 15 hour period. The THF is evaporated under high vacuum and the residue diluted with 10 ml of water, acidified to pH 3 with a 10% aqueous oxalic acid solution and extracted with three 100 ml portions of ether. The organic layer is washed with three 100 ml portions of water and 100 ml of brine. The product is dried over anhydrous magnesium sulfate and concentrated to give an oil.

This oil is purified on a CC-7 column, eluting with a gradient of distilled pentane/ether and filtered through a polycarbonate membrane. The solvents are evaporated under high vacuum for 12 days to give 131 mg of [1β,2β(5Z)3 ∝ (1E,3S*),4β]-7-[3-(3-hydroxy-4-phenyl-1-butenyl)-7-oxabicyclo[2.2.1]hept-2-yl]-5-heptenoic acid

EXAMPLE 3

[1β,2β(5Z)3 ∝ (1E,3S*),4β]-7-[3-(3-hydroxy-4-(3-thienyl)-1-butenyl]-7-oxabicyclo[2.2.1]hept-2-yl]-5-heptenoic acid

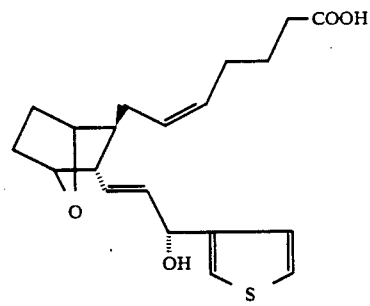

A. [1β,2β(5Z)3 ∝ (1E,3S*),4β]-7-[3-[3-oxo-4-(3-thienyl)-1-butenyl]-7-oxabicyclo[2.2.1]hept-2-yl]-5-heptenoic acid To 402.7 mg of freshly distilled diisopropylamine (3.98 mmole, 1.05 equiv.) in 30 ml of dry toluene at −78° C. is added 2.47 ml of a 1.6M solution of n-butyllithium in hexane (3.98 mmole, 1.05 equiv.). The mixture is stirred for 5 minutes, and to this mixture at −78° C. is added 1.034 g of 2-oxo-3-(3-thienyl)propyl dimethyl phosphonate (4.17 mmole, 1.1 equiv.). The mixture is warmed up to 25° C. while stirring. To this mixture at 25° C. is added 1.0 g of [1β,2β(5Z)3 ∝,4β]-7-[3-formyl-7-oxabicyclo[2.2.1]hept-2-yl]-5-heptenoic acid, methyl ester (prepared as described in Example 1) (3.79 mmole). After 3 hours, the reaction is quenched with 0.5 ml of glacial acetic acid and diluted with 300 ml of ether. The ethereal solution is washed with three 100 ml portions of a 5% sodium bicarbonate solution and 100 ml of brine. The organic layer is dried over anhydrous magnesium sulfate and concentrated to give 1.05 g of a crude oil. This oil used in the next step without purification.

[1β,2β(5Z)3 ∝ (1E,3S*),4β]-7-[3-[-Hydroxy-4-(3-thienyl)-1-butenyl]-7-oxabicyclo[2.2.1]hept-2-yl]-5-heptenoic acid, methyl ester and C. [1β,2β(5Z)3 ∝ (1E,3R*),4β]-7-[3-[-Hydroxy-4-(3-thienyl)-1-butenyl]-7-oxabicyclo[2.2.1]hept-2-yl]-5-heptenoic acid, methyl ester To a solution of 1.427 g of crude title A compound in 30 ml of dry methanol is added at 25° C., under an argon atmosphere, 1.416 g of cerium chloride containing 35% water (3.69 mmole, 1 equiv.). The reaction is stirred for 10 minutes at 25° C., cooled to 0° C. and 142.7 mg of sodium borohydride (3.69 mmole, 4 equiv.) is slowly added. After stirring for 10 minutes at 0° C., the reaction mixture is poured into 200 ml of saturated ammonium chloride. The mixture is extracted with three 100 ml portions of ether. The ethereal extracts are washed with three 100 ml portions of water and 100 ml of brine. The organic layer is dried over anhydrous magnesium sulfate and concentrated.

Separation and purification is achieved by HPLC eluting with 35% ethyl acetate in hexane to give 201 mg of title B compound and 107 mg of title C compound.

TLC of title B: silica gel; EtOAc/hexane (1:1); $R_f$ ~0.39.

TLC of title C: $R_f$ ~0.29.

D. [1β,2β(5Z)3 ∝ (1E,3S*),4β]-7-[3-(3-Hydroxy-4-(3-thienyl)-1-butenyl]-7-oxabicyclo[2.2.1]hept-2-yl]-5-heptenoic acid 201 mg of the title B alcohol ester (0.52 mmole) is dissolved in 20 ml of an 80% tetrahydrofuran-water solution, chilled to 0° C., and 5.2 ml of a 1N lithium hydroxide solution is added dropwise. The reaction is stirred at 0° C., then slowly warmed up to 25° C. over a 15 hour period. The THF is evaporated under high vacuum and the residue is diluted with 10 ml of water, acidified to pH 3 with a 10% aqueous oxalic acid solution and extracted with three 50 ml portions of ether. The organic layer is washed with three 30 ml portions of water and 30 ml of brine. The product is dried over anhydrous magnesium sulfate and concentrated to give an oil.

This oil is purified on a CC-7 silica gel column, eluting with a gradient of distilled pentane/ether and filtered through a polycarbonate membrane. The solvents are evaporated under high vacuum for 7 days to give 150 mg of [1β,2β(5Z)3 ∝ (1E,3S*),4β]-7-[3-[3-hydroxy-4-(3-thienyl)-1-butenyl]-7-oxabicyclo[2.2.1]hept-2-yl]-5-heptenoic acid (76.6%).

TLC: silica gel; ethyl acetate; $R_f$ ~0.53.

EXAMPLE 4

Ocular Hypotensive Effects in Rabbits

Experimental quantities of the compounds described in Examples 1-3 were added to a polysorbate carrier to produce final concentrations of 0.01%, 0.1%, 0.3%, or 1% as required. A group of 8 experimental rabbits was treated by administering one drop of each solution to the ocular surface. Intraocular pressure was measured by applanation pneumatonometry (Model 30RT, manufactured by Digilab) immediately before the time of administration and at 0. 5, 1, 2, 3, 4, and 6 hours, thereafter. In addition, the condition of the ocular surface was visually examined with special attention to the presence of ocular surface hyperemia. The following data were obtained and are summarized in Table 1.

TABLE 1

OCULAR HYPOTENSIVE EFFECT AT PREDETERMINED TIMES (HR)
AFTER PROSTAGLANDIN-LIKE 7-OXABICYCLO DERIVATIVES

| PG (DOSE %) | | TIME (HRS) | | | | | | |
|---|---|---|---|---|---|---|---|---|
| | | (0) | (0.5) | (1) | (2) | (3) | (4) | (6) |
| [1$\beta$,2$\beta$(5Z),3$\alpha$(1E,3S),4$\beta$]]-7-[3-(3-Cyclo-hexyl-3- | 0.01% | 0 | 5.5** | 5.8** | 1.7** | 0.5 | 2.1* | 1.80. |
| hydroxy-1-propenyl)-7-oxabicyclo-[2.2.1]hept-2- | 0.1% | 0 | 7.4** | 7.6** | 3.4** | 2.5* | 2.1* | 2.9* |
| yl]-5-heptenoic acid | 0.3% | 0 | 7.75** | 8.4** | 5.3** | 1.9 | 1.9 | 2.0 |
| [1$\beta$,2$\beta$(5Z),3$\alpha$(1E),4$\beta$]-7-[3-[3-Hydroxy-4-(3- | 0.1% | 0 | 3.6* | 4.1* | 2.5* | 2.25* | 1.4* | 0.6 |
| thienyl)-1-butenyl]-7-oxabicyclo[2.2.1]hept-2-yl]-5-heptenoic acid | 1.0% | 0 | 3.9* | 3.7* | 3.5* | 2.0* | 1.7* | 0.75 |
| [1$\beta$,2$\beta$(5Z),3$\alpha$(1E),4$\beta$]-7-[3-(3-Hydroxy-4-phenyl-1- | 0.1% | 0 | 2.6* | 3.1* | 1.8 | 1.25 | 0.06 | 0.25 |
| butenyl)-7-oxabicyclo[2.2.1]hept-2-yl]-5-heptenoic acid | 1.0% | 0 | 1.9* | 2.1* | 1.5* | 1.1 | 1.1 | 0.9* |

*$p < 0.5$; **$p < 0.01$ (Students paired t test)

The compounds show a pronounced decrease in intraocular pressure. [1$\beta$,2$\beta$(5Z)3 $\propto$ (1E,3S),4$\beta$]-7-[3-(3-cyclohexyl-3-hydroxy-1-propenyl)-7-oxabicyclo[2.2.1-]hept-2-yl]-5-heptenoic acid exhibited particularly potent activity with a >5 mmHg decrease in intraocular pressure with 0.01% dose. No ocular surface side effects, including ocular surface hyperemia, were observed for these examples.

EXAMPLE 5

Ocular Surface Inflammation in Guinea Pigs

Ocular inflammation is typically identified as changes in microvascular permeability and leukocyte infiltration. [1$\beta$,2$\beta$(5Z)3 $\propto$ (1E,3S),4$\beta$]-7-[3-(3-cyclohexyl-3-hydroxy-1-propenyl)-7-oxabicyclo[2.2.1]hept-2-yl]-5-heptenoic acid was examined as representative and its effects were compared to those of prostaglandin D$_2$ (PGD$_2$) and prostaglandin J$_2$ (PGJ$_2$). Solutions were prepared in Na$_2$CO$_3$ (2%) neutralized with HC$_l$ and made to a final concentration of 0.5%. Groups comprising six experimental animals received a 20 $\mu$l drop, contralateral eyes received an equal volume of vehicle as a control.

Increases in conjunctival microvascular permeability and histological studies were performed in male, albino, guinea pigs of the Hartley strain, weighing 350-450 g. This species was preferred for inflammation studies since the guinea pig and human conjunctiva appear to respond similarly to PGD$_2$. Conjunctival extravascular albumin accumulation was quantified by a previously described technique involving $^{51}$Cr-erythrocytes and $^{125}$I-bovine serum albumin (Woodward and Ledgard, 1985).

Leukocyte infiltration was determined by microscopic studies at 6 hour post-prostanoid administration. Immediately after sacrifice by intracardiac T-61, 10% neutral-buffered formalin was administered to the ocular surface. The globe and attached eyelid ring were then surgically excised intact and fixed in 10% neutral-buffered formalin for 24 hours at room temperature. Tissues were embedded in paraffin and two 6 $\mu$m sections were obtained per eye in such a manner as to prevent the same cell populations from being counted in both sections. The sections were stained by Luna's technique for eosinophil granules. Leukocyte numbers were expressed as the difference between treated and control tissues per high power field (h.p.f.).

The following data were obtained are summarized in Table 2.

TABLE 2

COMPARISON OF THE EFFECTS OF A PROSTAGLANDIN D-LIKE 7-OXABICYCLO DERIVIATIVE
WITH PGD$_2$ ON CONJUNCTIVAL MICROVASCULAR PERMEABILITY AND EOSINOPHIL
LEUKOCYTE INFILTRATION

| PROSTANOID (DOSE %) | MICROVASCULAR PERMEABILITY RESPONSE | ENSINOPHIL INFILTRATION (cells/hpf) + S.E.M. |
|---|---|---|
| PGD$_2$ | 0.89 $\pm$ 0.16 | 3.5 $\pm$ 0.7 |
| [1$\beta$-[2$\beta$,2$\beta$(5Z),3$\alpha$(1E,3S), 4$\beta$]-7-[3-(3-cyclohexyl-3-hydroxy-1-propenyl))-7-oxabicyclo [2,2,1]hept-2-yl]-5 heptenoic acid (0.5%) | 0.09 $\pm$ 0.03 | 0.1 $\pm$ 0.4 |

PGD$_2$ typically produces an increase in conjunctival microvascular and eosinophil infiltration and these pathological effects would greatly limit PGD$_2$ as anti-glaucoma therapy. PGJ$_2$ also caused a similar leukocyte infiltrate. In contrast, a PGD-like 7-oxabicyclo derivative does not cause ocular surface pathology at a dose that greatly exceeds that required to cause pronounced decreases in intraocular pressure.

The foregoing description details specific formulations and methods that can be employed to practice the present invention. Having detailed specific compositions for the topical formulations of the present invention and specific instructions for their use, the art skilled will well enough know to devise other formulations and how to adapt the treatment (formulations, doses) to a special situation. Thus, however detailed the foregoing may appear in text, it should not be construed as limiting the overall scope hereof; rather the ambit of the present invention is to be governed only by the lawful construction of the appended claims.

I claim:

1. A method of treating ocular hypertension which comprises administering to a mammal having ocular hypertension a therapeutically effective amount of a compound of formula (I)

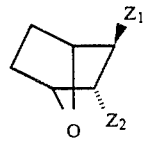

or an isomer thereof, wherein $Z_1$ is an $-RCOOR_1$ group in the $\beta$ configuration, wherein R is an alkyl or alkenyl group having up to 10 carbon atoms, $R_1$ is selected from the group consisting of hydrogen, an aliphatic radical of from one to 10 carbon atoms and a cation which forms a pharmaceutically acceptable salt; $Z_2$ is $-CH=CH-CH(OR_2)R_3$ in the $\alpha$ configuration, wherein $R_2$ is hydrogen or an acyl group having from one to 6 carbon atoms, and $R_3$ is selected from the group consisting of cycloalkyl having 5 or 6 carbon atoms, aryl and aralkyl each having 5 or 6 carbon atoms in the aryl moiety.

2. The method of claim 1 wherein $R_3$ is cyclohexane.

3. The method of claim 1 wherein $R_2$ is hydrogen.

4. The method of claim 2 wherein R is an alkyl or alkenyl group having 4 to 8 carbon atoms.

5. The method of claim 4 wherein R is an alkyl or alkenyl group having 6 carbon atoms.

6. The method of claim 1 wherein $Z_1$ is 7-carboxyl-hept-2-yl.

7. The method of claim 1 wherein $Z_2$ is 3-cyclohexyl-3-hydroxy-1-propenyl.

8. The method of claim 1 wherein $Z_2$ is 3-hydroxy-4-phenyl-1-butenyl.

9. The method of claim 1 wherein $Z_2$ is 3-hydroxy-4-(3-thienyl)-1-butenyl.

10. The method of claim 1 wherein said compound of formula (I) is selected from the group consisting of

[1$\beta$,2$\beta$(5Z),3$\alpha$(1E,3S*),4$\beta$]-7-[3-Cyclohexyl-3-hydroxy-1-propenyl)-7-oxabicyclo[2.2.2]hept-2-yl]-5-heptenoic acid;

[1$\beta$,2$\beta$(5Z),3$\alpha$(1E,3S*),4$\beta$]-7-[3-(3-hydroxy-4-phenyl-1-butenyl)-7-oxabicyclo[2.2.1]hept-2-yl]-5-heptenoic acid;

[1$\beta$,2$\beta$(5Z),3$\alpha$(1E,3S*),4$\beta$]-7-[3-[3-hydroxy-4-(3-thienyl)-1-butenyl]-7-oxabicyclo[2.2.1]hept-2-yl]-5-heptenoic acid, and pharmaceutically acceptable esters and salts of these compounds.

* * * * *